United States Patent [19]

Ross

[11] 4,107,435

[45] Aug. 15, 1978

[54] PROCESS FOR ω-AMINO-2-HYDROXYALKYL DERIVATIVES OF AMINOGLYCOSIDE ANTIBIOTICS

[75] Inventor: Barry C. Ross, Birchington, England

[73] Assignee: Pfizer Inc., New York, N.Y.

[21] Appl. No.: 767,657

[22] Filed: Feb. 10, 1977

[30] Foreign Application Priority Data

Feb. 25, 1976 [GB] United Kingdom ............... 7529/76

[51] Int. Cl.² .................. C07D 263/24; C07D 265/06
[52] U.S. Cl. ........................................ 544/97; 536/4; 536/10; 536/17; 260/307 C
[58] Field of Search ................... 544/97; 260/307 C

[56] References Cited

U.S. PATENT DOCUMENTS 2,399,118  4/1946  Homeyer ..................... 260/307 C

OTHER PUBLICATIONS

Skulsi et al., Chemical Abstracts, vol. 51, cols. 371 to 372 (1957).

*Primary Examiner*—John D. Randolph
*Attorney, Agent, or Firm*—Connolly and Hutz

[57] ABSTRACT

1-N-(ω-Amino-2-hydroxyalkyl) derivatives of aminoglycoside antibiotics are prepared by reductive alkylation of the parent antibiotic, or a partially protected derivative thereof, with a 6-dihydroxymethyltetrahydro-1, 3-oxazin-2-one or 5-dihydroxymethyloxazolidin-2-one, followed by hydrolysis, and, if necessary, followed by removal of any remaining protecting groups. The products of the process of this invention are known antibacterial agents.

6 Claims, No Drawings

PROCESS FOR ω-AMINO-2-HYDROXYALKYL DERIVATIVES OF AMINOGLYCOSIDE ANTIBIOTICS

BACKGROUND OF THE INVENTION

This invention relates to a process for the preparation of antibacterial aminoglycoside derivatives and with intermediates for use in said process. More particularly it is concerned with a novel process for the preparation of 1-N-[ω-amino-2-hydroxyalkyl] and 1-N-[ω-(N-benzylamino-)-2-hydroxyalkyl] derivatives of aminoglycoside antibiotics. Said 1-N-[ω-amino-2-hydroxyalkyl] derivatives are known antibacterial agents, described in West Germany Offenlegungsschrift 2,547,738 and Belgian Pat. No. 818,431, and said 1-N-[ω-(N-benzylamino)-2-hydroxyalkyl] derivatives are useful as intermediates to said 1-N-[ω-amino-2-hydroxyalkyl] compounds. Additionally, this invention is concerned with certain cyclic urethane compounds which are also useful as intermediates in the process of the invention.

Previous procedures for the introduction of an ω-amino-2-hydroxyalkyl group onto the 1-amino group of an aminoglycoside antibiotic have required a multistage process. For example, in one process described in West German Offenlegungsschrift 2,547,738, the group is introduced by acylation with an ω-amino-2-hydroxycarboxylic acid derivative having a protected amino group. The amino-protecting group is then removed and the amide bond is reduced to give the desired product. Other methods are described in Belgian Pat. No. 818431.

It is an object of this present invention to provide a convenient process for the introduction of an ω-amino-2-hydroxyalkyl substituent onto the 1-amino group of aminoglycoside antibiotics, which has the additional advantage of allowing the stereochemistry of the substituent to be readily controlled.

SUMMARY OF THE INVENTION

According to the invention there is provided a process for the preparation of compounds of the formula

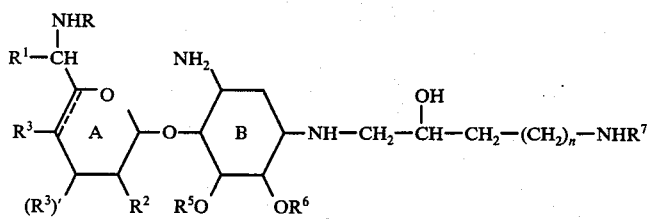
(I)

wherein R is selected from the group consisting of hydrogen and alkyl having from one to four carbon atoms;
$R^1$ is selected from the group consisting of hydrogen and methyl;
$R^2$ is selected from the group consisting of hydroxy and amino;
$R^3$ and $(R^3)'$ are always the same and they are selected from the group consisting of hydrogen and hydroxy;
$R^5$ and $R^6$ are each selected from the group consisting of hydrogen and a glycosyl group, provided that $R^5 R^6$ are always different;
$R^7$ is selected from the group consisting of hydrogen and benzyl;

the broken line represents an optional second bond, provided that the optional second bond is present only when each of $R^3$ and $(R^3)''$ is hydrogen;
and n is 0 or 1;
said process comprising:
(a) reductive alkylation of a compound of the formula

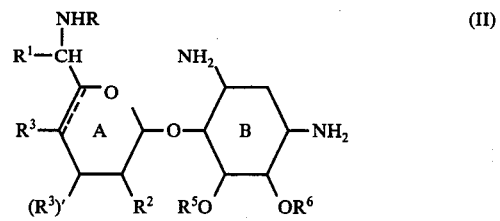
(II)

wherein R, $R^1$, $R^2$, $R^3$, $(R^3)'$, $R^5$ and $R^6$ are as previously defined, or a derivative of the compound of the formula II in which one or more of the amino groups other than the 1-amino group carries an amino protecting group, with a cyclic urethane of the formula

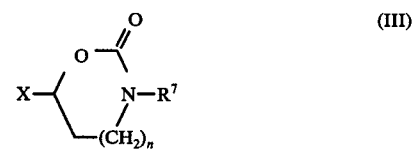
(III)

wherein X is selected from the group consisting of formyl and dihydroxymethyl, and $R^7$ is as defined previously; and
(b) hydrolysis of the product of step (a), and removal of any remaining amino protecting groups if necessary, to give the corresponding compound of the formula I.

The compounds of the formula I, wherein $R^7$ is hydrogen are known antibacterial agents; the compounds of the formula I, wherein $R^7$ is benzyl are intermediates to the compounds of the formula I, wherein $R^7$ is hydrogen. The benzyl group is removed by catalytic hydrogenolysis.

When $R^5$ represents a glycosyl group, such a group is a pentofuranosyl group which may optionally be linked to further hexopyranosyl groups by a glycosidic linkage. Preferred examples of such groups are those occurring in ribostamycin, neomycin and lividomycin in which the glycosyl groups have the following structures respectively:

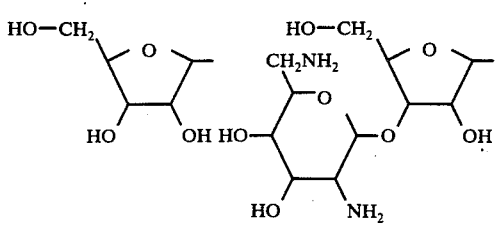

and

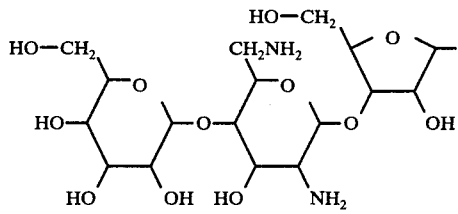

When $R^6$ represents a glycosyl group, such a group is a hexopyranosyl group containing two or more hydroxyl groups and optionally containing an amino or methylamino group. Preferred examples of such glycosyl groups are those occurring in kanamycin and gentamicin in which the glycosyl groups have the following structures respectively:

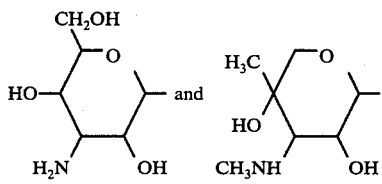

The optional protection of free amino groups in the compound of formula II in the course of the process of the invention can be achieved by reaction with a reagent selective for primary amino groups and easily removable therefrom subsequently by conventional techniques, for example by hydrolysis or hydrogenolysis. Examples of suitable protecting groups are the formyl, acetyl, trifluoroacetyl, methoxycarbonyl, t-butyloxycarbonyl, benzyl and benzyloxycarbonyl groups, especially the formyl group.

However, a preferred embodiment of this invention is to provide a process, and intermediates therefor, for the preparation of a compound of the formula I, wherein R is selected from the group consisting of hydrogen and alkyl having from one to four carbon atoms; $R^1$ and $R^5$ are each hydrogen; $R^2$ is selected from the group consisting of hydroxy and amino; each of $R^3$ and $(R^3)'$ is hydroxy; $R^7$ is selected from the group consisting of hydrogen and benzyl; and $R^6$ is 3-amino-3-deoxy-α-D-glucopyranosyl, viz:

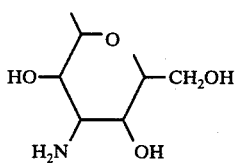

The preferred starting materials of formula II are those compounds of the formula

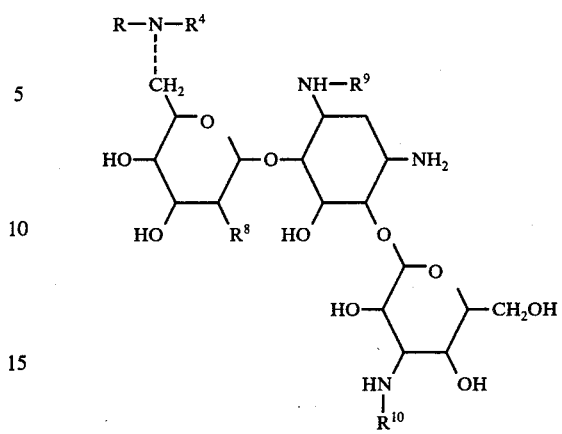

wherein R is selected from the group consisting of hydrogen and alkyl having from one to four carbon atoms; $R^4$, $R^9$ and $R^{10}$ are each selected from the group consisting of hydrogen and formyl; and $R^8$ is selected from the group consisting of hydroxy, amino and formamido.

DETAILED DESCRIPTION OF THE INVENTION

Step (a) of the process of the present invention is a conventional reductive alkylation reaction of the 1-amino group in a compound of the formula II, using a compound of the formula III as the aldehyde component. Thus, the compound of the formula III can be used either as the free aldehyde (X is formyl) or in the functionally-equivalent hydrated form (X is dihydroxymethyl). As is well-known in the art, reductive alkylation of an amine with an aldehyde is itself a two-step procedure. In the first step, the compound of the formula II is contacted with at least about 1 molar equivalent, and preferably a slight excess, of the compound of the formula III, to form a Schiff's base. In the second step, the Schiff's base is reduced to give a compound of the formula IV

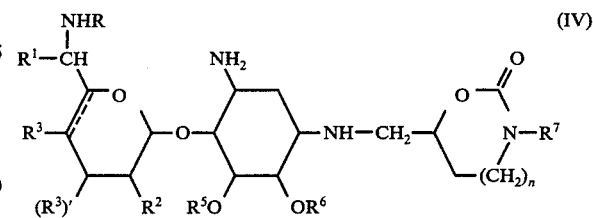

(IV)

wherein R, $R^1$, $R^2$, $R^3$, $(R^3)'$, $R^5$, $R^6$, $R^7$ and $n$ are as defined previously, or the corresponding derivative of the formula IV in which one or more of the amino groups other than the 1-amino group carries an amino protecting group.

In practice, the reductive alkylation can be carried out in a true stepwise fashion, by allowing formation of the Schiff's base to proceed substantially to completion before performing the reductive step. Alternatively, the reducing agent can be added to the mixture of the compound of the formula II and the compound of the formula III, in a suitable reaction-inert solvent, thus allowing the Schiff's base to be reduced in situ as soon as it is formed. The reduction may suitably be effected using sodium borohydride, or preferably sodium cyanoborohydride, as the reducing agent and is conveniently performed by adding the latter to the reaction mixture at a pH generally between 4 and 7, thereby enabling the reaction to be performed effectively in a single stage. Alternatively the mixture of the aminoglycoside II and the stepwise urethane of formula III may be subjected to a conventional catalytic hydrogenation using for example a palladium-on-charcoal or a platnium catalyst. The whole reaction may conveniently be performed with the reactants dissolved in a reaction-inert solvent, e.g. water, aqueous methanol, aqueous ethanol, aqueous dioxan, aqueous tetrahydrofuran or the like, at a temperature from about 0° to about 100° C. The period within which the reaction goes substantially to completion naturally depends on the nature of the reactants, solvent and the temperature employed, but it is found that the reaction between the aminoglycoside of formula II and the cyclic urethane of formula III in the presence of a slight excess of sodium cyanoborohydride at a pH between 4 and 7 is generally substantially complete within three or four days when performed in a reaction-inert solvent at a temperature of 40°–50° C. The product can be isolated, after neutralizing the reaction mixture, by conventional techniques, e.g. by evaporation followed by extraction and crystallization or by ion-exchange chromatography. Alternatively the crude reaction mixture may be used directly in the next stage of the process.

Step (b) of the process of this invention, in which the cyclic urethane ring is opened, is achieved by a hydrolysis reaction in which the compound of formula IV is preferably treated with aqueous base. The reaction is conveniently performed with the compound of formula IV dissolved in a reaction inert solvent, e.g. water, aqueous methanol, aqueous ethanol, aqueous dioxan, aqueous tetrahydrofuran or the like, and can be effected using an alkali metal hydroxide or an alkaline earth metal hydroxide, such as sodium, potassium or barium hydroxide. The reaction can be performed at a temperature from about 0° C to about 100° C., and it takes up to 5 days, depending upon the particular nature of the reactants and the temperature employed. It is found that, when the reaction is performed using 1N sodium hydroxide solution to effect the hydrolysis, the reaction is substantially complete within 48 hours at room temperature. The product can conveniently be isolated by neutralizing the solution and evaporation. The crude product can then be further purified, if desired, by conventional means, for example by ion-exchange chromatography.

The cyclic urethane derivative of formula III can be reacted with any aminoglycoside derivative of formula II having a free 1-amino group. If other free amino groups are present in the molecule these will also react; however, if only a slight excess of the cyclic urethane is used, the desired product can be readily separated from the other positional-isomers, and from products substituted on more than one amino group, which are present in the reaction mixture, for example by conventional chromatography. It is, however, desirable to protect some, or preferably all, of the other free amino groups present in the compound of formula II, prior to reductive alkylation in order to facilitate final isolation of the compound of formula I. In particular it is desirable to protect at least the 6'-amino group. Thus as a final stage in the preparation of compounds of the formula I it will be necessary to remove any amino protecting groups which have not been removed during step (b), the hydrolysis step, of the aforesaid reaction scheme. Any remaining amino protecting groups are removed in conventional manner for that particular protecting group.

A particularly preferred protecting group for the compounds of formula II is the formyl group, which is particularly advantageous because it is removed in the second stage of the process of the invention, i.e. during the hydrolysis stage. Also suitable are the tertiary-butyloxycarbonyl group which can be removed under acidic conditions, for example by treatment with anhydrous trifluoroacetic acid at room temperature for up to 30 minutes, and the benzyloxycarbonyl group which may be removed by catalytic hydrogenation e.g. by hydrogenation in aqueous acetic acid solution in the presence of palladium on charcoal catalyst at 30° C. and at a pressure of 50 p.s.i. Hydrogenolysis is normally complete under these conditions in less than 12 hours.

Particularly preferred protected aminoglycoside derivatives of formula II for use in the process of the invention are 3,3'', 6'-tri-formylkanamycin A and 2', 3,3'',6'-tetra-N-formylkanamycin B. 6'-N-benzyloxycarbonylkanamycin A and 6'-N-t-butyloxycarbonylkanamycin A can also be used advantageously.

As indicated hereinbefore, the compounds of the formula I, wherein $R^7$ is benzyl, are useful as intermediates to the corresponding compounds of the formula I, wherein $R^7$ is hydrogen. The benzyl group can be removed by catalytic hydrogenolysis, for example by subjecting the compound, wherein $R^7$ is benzyl, to catalytic hydrogenation, in a suitable solvent such as a mixture of water, methanol and acetic acid, at 60 psi, for several hours at about 60° C. When the reaction is complete the reaction mixture is worked-up in conventional manner e.g. by filtration and evaporation of the solvent. The crude product can then be purified if desired in the usual way, e.g. by recrystallization from a suitable solvent or by chromatography.

As will be appreciated by one skilled in the art each of the substituents attached to rings A and B in the compounds of the formulae I and II can exist in one of two stereochemical orientations. However, this invention provides a process for the alkylation of the 1-amino group of compounds of the formula II with substituents having orientations corresponding to those found in the naturally-occurring aminoglycosides, such as the kanamycins, the gentamicins, tobramycin, ribostamycin, the neomycins and lividomycin. Additionally the ω-amino-2-hydroxyalkyl substituent on the 1-amino group of a compound of the formula I can exist in two isomeric forms, the (R)- and the (S)-configuration. The process of the present invention provides compounds of the formula I, wherein the ω-amino-2hydroxyalkyl side chain is in the (R)-configuration, compounds of the formula I, wherein the side chain is the (S)-configuration, and mixtures thereof.

The cyclic urethane intermediates of formula III are themselves novel compounds according to the invention. They may be prepared in several stages from readily available aldopentose or aldohexose sugars, or 2-deoxy sugars, by a process which involves, first, reductive amination of the sugar with ammonia or an amine of the formula $R^7NH_2$ where $R^7$ is benzyl, secondly formation of a cyclic urethane ring by reaction with an arylchloroformate followed, if necessary, by treatment with a base, and finally oxidation to generate the aldehyde function.

In practice it is found that the compound of the formula III is generally isolated in its hydrated form in which X is (HO)₂CH— although it will be realized that this is a functional equivalent of a compound in which X is O=CH— and the invention includes both forms of the compound of the formula III. It is a feature of this invention that the stereochemistry of the carbon atom to which the substituent X is attached in the cyclic urethane of the formula III can be readily controlled, thus enabling the stereochemistry of the 1-N-[ω-amino-2-hydroxyalkyl] substituent in the final product of the formula I to be readily controlled.

The preparation of compounds of formula III, wherein n is 1, is exemplified by the preparation of 3-benzyl-6-(S)-dihydroxymethyl-tetrahydro-1,3-oxazine-2-one (IX) from 2-deoxy-D-ribose. The preparation is represented as shown in Reaction Scheme 1, in which R⁷ is a benzyl group.

REACTION SCHEME 1

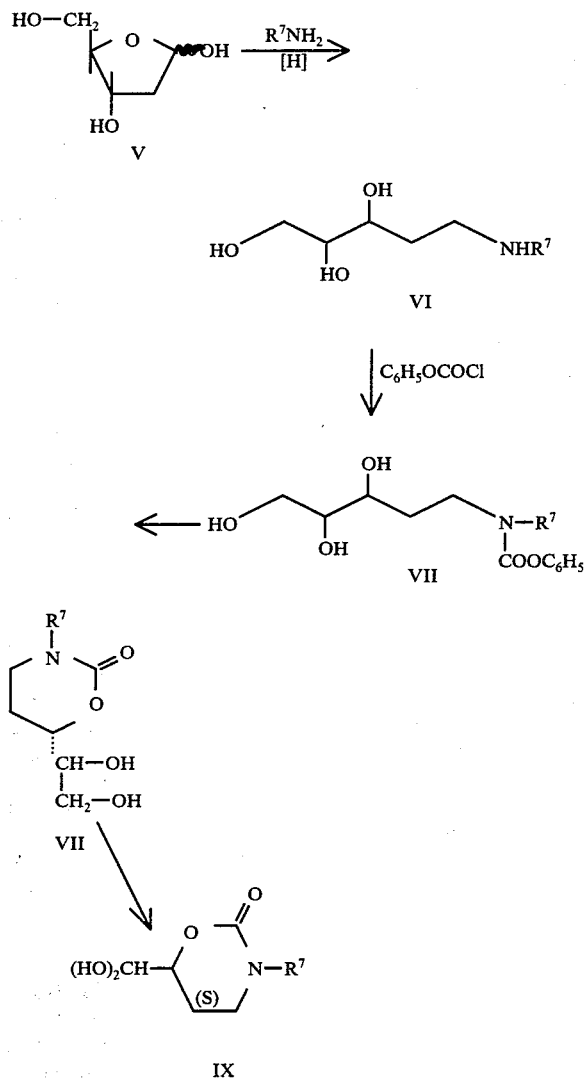

Thus as a first step in the preparation, 2-deoxy-D-ribose V is reacted with a slight excess of benzylamine in the presence of a reducing agent, e.g. sodium cyanoborohydride at pH 5, or alternatively with concomitant catalytic hydrogenation in a conventional manner. Sodium cyanoborohydride is a preferred reagent, and in this case the reaction can conveniently be performed with the reactants dissolved in a reaction inert solvent, e.g. water and is generally complete within 24 hours at room temperature. Alternatively the reduction can be performed by catalytic hydrogenation at 50° C. and 50 psi pressure in the presence of a platinum oxide catalyst. The product VI can be isolated by conventional techniques, if desired, but is conveniently used directly in the second stage of the process, the reaction mixture being treated directly with a slight excess of an aryl-chloroformate, preferably phenyl chloroformate. This reaction is preferably performed with cooling e.g. at a temperature between 0° and 10° C and is generally complete within several hours. The product VII can be isolated by conventional techniques e.g. by extraction with an organic solvent, for example with ethyl acetate. The product obtained after removal of the solvent is generally sufficiently pure for use in the next part of the process, but can be further purified if desired, e.g. by recrystallization or chromatography. The cyclization is completed by treating the compound of the formula VII, dissolved in a suitable solvent with a strong base. For example, the cyclization reaction can be performed with potassium t-butoxide in t-butanol or preferably with sodium hydroxide in water or aqueous ethanol, or alternatively with sodium hydride in a mixture of t-butanol and dioxan. The reaction is conveniently performed at room temperature and is generally complete within 24 hours. The solution is neutralized and the product VIII can then be isolated by evaporation and purified. The second stage of the process, and the cyclization reaction, may also be achieved with p-nitrophenyl chloroformate, in this case ring closure takes place simultaneously without the need for a separate base treatment step. The final stage of the process involves the oxidative cleavage of the diol substituent present in the compound of formula VIII, to form the aldehyde function, and this can be achieved by various methods well known to those skilled in the art. In practice the oxidation can conveniently be achieved using an aqueous solution of sodium metaperiodate. The reaction is generally complete within a few minutes at room temperature and the product IX which in this case precipitates from solution in substantially pure form can be collected by filtration and dried.

The intermediate IX when used in the process of the invention for the preparation of compounds of formula I will give rise to a compound where R⁷ is benzyl, n is 1 and the asymmetric carbon atom in the 1-amino side-chain has the (S)-configuration. On subsequent hydrogenation this provides a 1-N-[(S)-4-amino-2-hydroxybutyl]aminoglycoside derivative.

A cyclic urethane in which n is 1 and R⁷ is hydrogen is prepared using the method outlined in Reaction Scheme 1, but using the corresponding compound of the formula VI, wherein R⁷ is hydrogen.

It will be appreciated by one skilled in the art that it is the stereochemistry at C-3 in the starting 2-deoxy-D-ribose which controls the stereochemistry at the carbon atom to which the substituent X is attached in the compound of the formula IX. Accordingly, any 2-deoxypentose, or higher monosaccharide which lacks a 2-hydroxy group ad has C-3 in the (S)-configuration, can be used to prepare a compound of the formula III, wherein n is 1 and the carbon atom to which X is attched has the (S)-configuration. In like manner, any aldopentose, or higher monosaccharide, which lacks a 2-hydroxy group and has C-3 in the (R)-configuration, can be used to prepare a compound of the formula III, wherein n is 1 and the carbon atom to which X is attached has the (R)-configuration.

In order to prepare compounds of the formula III, wherein n is 0, it is necessary to start with an aldotetrose, or higher monosaccharide, in which the 2-hydroxy group is present. This is exemplified in Reaction Scheme 2, wherein D-ribose is converted into the compound of the formula III, wherein n is 0, $R^7$ is benzyl and the carbon atom to which X is attached has the (S)-configuration. Each of the steps of Reaction Scheme 2 is carried out in a manner analogous to the corresponding step in Reaction Scheme 1.

REACTION SCHEME 2

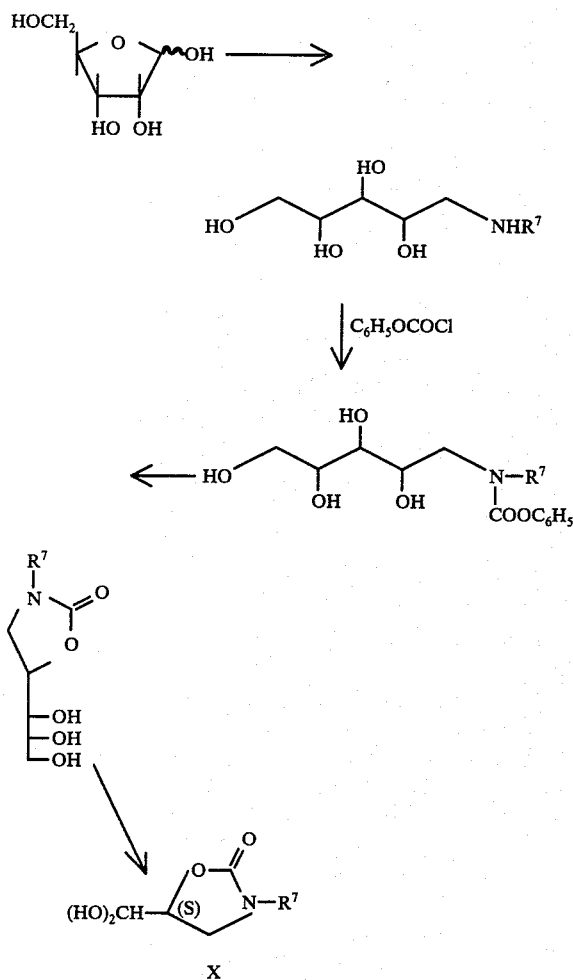

Repetition of Reaction Scheme 2, but using an aldopentose with C-2 in the (R)-configuration leads to the enantiomer of the compound of the formula X.

As indicated hereinbefore, the process of the present invention provides a method for the introduction of an ω-amino-2-hydroxyalkyl side chain onto the 1-amino group of an aminoglycoside antibiotic, in such a manner that the stereochemistry of the carbon atom in the side-chain (i.e. the carbon atom carrying the 2-hydroxy group) can be controlled. Thus, when the carbon atom carrying the substituent X in the compound of the formula III has the (S)-configuration, the carbon atom carrying the 2-hydroxy group in the compound of the formula I so produced will have the (S)-configuration. In like manner, when the carbon atom carrying the X substituent in the compound of the formula III has the (R)-configuration, the carbon atom carrying the 2-hydroxy group in the compound of the formula I so produced will have the (R)-configuration.

The aminoglycoside or protected aminoglycoside derivative of formula II are either known compounds which are prepared as described in the prior art, ot they are analogues or homologues of prior art compounds, which are prepared by methods analogous to those described in the prior art. For example 3,3'',6'-tri-N-formyl-kanamycin A is described in Belgian Pat. No. 817,546. Derivatives in which the 6'-amino group is protected are well known and their preparation is described, for example in British Patent Specification No. 1401220 and in West German Patent Nos. 2,311,524, 2,350,169 and 2,512,587.

The following Examples are given solely for the purpose of further illustration. Temperatures are given in degrees Centigrade. "Amberlite" is a Registered Trademark, and refers to an anion-exchange resin having a polystyrene matrix, cross-linked with 3–5% of divinylbenzene, which contains quaternary ammonium groups which have been introduced by chloromethylation followed by amination.

EXAMPLE 1

3-Benzyl-6(S)-dihydroxymethyltetrahydro-1,3-oxazin-2-one (A) A solution of benzylamine (2.14 g, 0.02 moles) in water (25 ml) was adjusted to pH5 with 5N hydrochloric acid. 2-Deoxy-D-ribose (1.34 g, 0.01 mole) and sodium cyanoborohydride (0.062 g, 0.01 mole) were added and the solution was allowed to stand for 15 hours at room temperature. The pH of the solution was adjusted to 10 with sodium carbonate and the mixture was washed several times with ethyl acetate. The aqueous solution was cooled to 0° C, and phenyl chloroformate (1.7 g., 0.011 mmoles) in dioxan (15 ml) was added with stirring. After 3 hours at 0° C., the reaction was allowed to warm to room temperature, the pH was adjusted to 7 by the addition of 5N hydrochloric acid and the mixture was extracted with ethyl acetate. The organic extract was dried over magnesium sulphate and evaporated under reduced pressure to yield 1,2(S),3(S)-trihydroxy-5-[N-phenoxycarbonyl-N-benzylamino]-pentane (2.1 g.) as an oil which slowly solidified on standing. δ (CDCl$_3$ + D$_2$O) 7.2 (10 H, m); 4,5 (2H, s); 3,5 (6 H,m) 1.8 (2H,m). $\nu_{max.}$ (film) 3400, 1705, 1600 cm$^{-1}$.

(B) The product from A (1.5 g.), dissolved in a mixture of t-butanol (50 ml.) and dioxan (50 ml.), was stirred at room temperature and treated with sodium hydride (0.34 g., as 70% dispersion in oil). After 24 hours the pH was adjusted to 7 with 5N hydrochloric acid and the solution was evaporated to dryness. The product was extracted with ethanol and the inorganic residue was discarded. Repeated evaporation and extraction into ethanol gave a product free from inorganic material. The residue was finally partitioned between ethyl acetate and water and the aqueous layer was separated and evaporated under reduced pressure to yield 3-benzyl-6-(S)-(1',2'-dihydroxyethyl)tetrahydro-1,3-oxazin-2-one (0.3 g.) as an oil. δ (D$_2$O) 7.3 (5H, s); 4.4 (2H, s); 4.2 (1H, m); 3.7 (3H, m); 3.1 (2H, m); 1.9 (2H, m). $\nu_{max.}$ (film) 3400, 1660 cm$^{-1}$.

(C) The product from B (0.2 g) in water (10 ml) was treated with an aqueous solution of periodic acid (0.2 g), taken to pH 5 with 5N sodium hydroxide, at room temperature. After a few minutes a precipitate formed and then the reaction mixture was allowed to stand for 2 hours. The solid precipitate was then collected by filtration, washed with a little water and dried to yield 3-benzyl-6-(S)-dihydroxymethyl-tetrahydro-1,3-oxazin-2-one (0.15 g), m.p. 120°. (Found: C, 60.0; H, 6.3; N, 5.8. $C_{12}H_{15}NO_4$ requires C, 60.7; H, 6.3; N, 5.9%). $\delta$ (DMSO-$d_6$) 7.3 (5H, s); 6.1 (2H, d, exchangeable with $D_2O$); 4.9 (1H, m); 4.5 (2H, s); 4.0 (1H, m) 3.2 (2H, m); 2.0 (2H, m). $\nu_{max.}$ 3300, 1670 cm$^{-1}$ $[\alpha]_D + 71.5°$ (C, 1 in methanol).

EXAMPLE 2

3-Benzyl-6-(R)-dihydroxymethyltetrahydro-1,3-oxazin-2-one

The title compound is prepared using the procedure of Examples 1, but using 2-deoxy-D-xylose in place of the 2-deoxy-D-ribose.

EXAMPLE 3

3-Benzyl-6(S)-dihydroxymethyltetrahydro-1,3-oxazin-2-one (A) 2-Deoxy-D-ribose (100 g; 0.746 mole) and benzylamine (96 g; 0.897 mole) were dissolved in methanol (400 ml) and water (40 ml) and hydrogenated at 50° C and 50 p.s.i. in the presence of platinum oxide catalyst (4.0 g) until hydrogen uptake was complete. The catalyst was filtered off and the filtrate was cooled in an ice bath. The resulting crystalline precipitate was collected, washed with cold methanol, and dried to give 5-(benzylamino)-1,2(S),3(S)-trihydroxypentane (100 g; 59.5% yield). A sample was recrystallized from ethyl acetate, m.p. 117°–118.5° C, $\delta$ (DMSO-$D_6$) 7.3 (5H, s); 3.9 (3H, m, exchangeable with $D_2O$); 3.7 (2H, s); 3.4 (4H, m); 2.6 (2H, m); 1.6 (2H, m). $\nu_{max}$ 3370, 3310, 3290 cm$^{-1}$. (Found: C, 64.3; H, 8.5; N, 6.1. $C_{12}H_{19}NO_3$ requires: C, 64.0; H, 8.5; N, 6.2%). (A).

(B) The product from (A) (95 g; 0.422 mole) was suspended in dimethylformamide (570 ml) containing triethylamine (122 ml; 0.844 mole) and cooled to −10° C. Phenyl chloroformate (66.1 g; 0.422 mole) was added over 30 minutes maintaining the temperature in the range −5° C to −10° C. After 2 hours at this temperature, and 2 hours at room temperature, the reaction mixture was concentrated by evaporation under reduced pressure. The residue was dissolved in water and extracted with ethyl acetate. The organic layer was backwashed with water, dried over magnesium sulphate and evaporated under reduced pressure to give 1,2(S),3(S)-trihydroxy-5-(N-phenoxycarbonyl-N-benzylamino)pentane as a thick oil (138 g; 95% yield) which slowly solidified on standing. M$^+$ found $^m/e$ 252, $C_{19}H_{23}NO_5$-$OC_6H_5$ requires $^m/e$ 252. $\delta$ as for Example 1(A0).

(C) The product from (B) (110 g; 0.32 mole) was dissolved in industrial methylated spirits (258 ml) and a solution of sodium hydroxide (25.8 g; 0.64 mole) in water (258 ml) added. The solution was stirred at room temperature for 2 hous and then neutralized with dilute hydrochloric acid. Most of the organic solvent was removed by evaporation and the aqueous residue washed with ether and evaporated to dryness under reduced pressure. The residue was suspended in industrial methylated spirits, filtered to remove inorganic material, and the filtrate was evaporated. The semi-solid residue was slurried with petroleum ether, filtered and dried to give 3-benzyl-6-(S)-(1,2-dihydroxyethyl)tetrahydro-1,3-oxazin-2-one (77 g; 96% yield) m.p. 100.5°–102.5° C. M$^+$ found $^m/e$ = 251, $C_{13}H_{17}NO_4$ requires $^m/e$ = 251. $\delta$ ($D_2O$) as for Example 1(B). (Found: C, 62.0; H, 6.9; N,5.5. $C_{13}H_{17}NO_4$ requires C, 62.1; H, 6.8; N, 5.6%).

(D) The product from (C) (75 g; 0.299 mole) was dissolved in water (1350 ml) and cooled to 0° to 5° C. A clarified solution of sodium metaperiodate (63.55 g; 0.299 mole) in water (400 ml) was then added at this temperature over 15 minutes. After stirring for a further 30 minutes at 0° to 5° C the precipitated solid was collected, washed with water and dried at 50° C in vacuum to give 3-benzyl-6-(S)-dihydroxymethyl-tetrahydro-1,3-oxazin-2-one (52.3 g; 73.7% yield), m.p. 118°–120° C (Found: C, 60.6; H, 6.3; N, 5.9. $C_{12}H_{15}NO_4$ requires C, 60.7; H, 6.3; N, 5.9%. $\delta$ (DMSO-$d_6$) as for Example 1(C).

EXAMPLE 4

5(S)-Dihydroxymethyloxazolidin-2-one (A) 1-Amino-1-deoxy-D-ribitol (2.1 g, 0.014 mole prepared from D-ribose as described by Wolfron et. al. *J. Org. Chemi.* 23, 571 [1958]) was dissolved in water (30 ml), and sodium carbonate (2.9 g, 28 mole) and a solution of p-nitrophenyl-chloroformate (3.2 g, 0.016 mole) in acetone (10 ml) were added at 0° C. The solution was stirred and allowed to stand at room temperature overnight. The solution was acidified with 5N hydrochloric acid and extracted several times with ethyl acetate. The aqueous phase was evaporated and the residue extracted with ethanol. Chromatography on silica eluting with a gradient of chloroform and ethanol gave 5-(S)-(1′,2′,3′-trihydroxypropyl)-1,3-oxazolidin-2-one (0.7 g) an an oil.

Found: C, 40.1; H, 6.4 N, 6.7. $C_6H_{11}NO_5$ requires C, 40.7; H, 6.3; N, 7.9%.

(B) The product from (A) in water (2 ml) was treated with periodic acid (1.5 g), the pH was adjusted to 5 with 5N sodium hydroxide and the solution allowed to stand at room temperature for 48 hours. The solution was evaporated and the organic material extracted with ethanol. Chromatography on silica gave 5-(S)-dihydroxymethyl-oxazolidin-2-one (0.4 g) as an oil. Rf 0.76 in chloroform-methanol(1:1). $^m/e$ 86, $C_4H_7NO_4$—CH(OH)$_2$ requires $^m/e$ 86. $\delta$ ($D_2O$) 5.2 (1H, m); 4.6 (HOD and 1H, m); 3.5 (2H, m).

EXAMPLE 5

3-Benzyl-5(S)-dihydroxymethyloxazolidin-2-one

The title compound is prepared from 1-benzylamino-1-deoxy-D-ribitol (cf. Kagan et al., *Journal of the American Chemical Society*, 79, 3541 [1957]) and 4-nitrophenyl chloroformate, followed by oxidation with periodic acid, according to the procedure of Example 4.

EXAMPLE 6

5(R)-Dihydroxymethyloxazolidin-2-one

The title compound is prepared by repeating Example 4, but using 1-amino-1-deoxy-D-arabinitol in place of 1-amino-1-deoxy-D-ribitol. 1-Amino-1-deoxy-D-arabinitol is prepared from D-arabinose, via reductive alkylation of benzylamine, followed by catalytic hydrogenolysis of the benzyl group Kagan, *Journal of the American Chemical Society*, 79, 3541 [1957]).

EXAMPLE 7

6-(S)-Dihydroxymethyltetrahydro-1,3-oxazin-2-one (A) A solution of benzylamine (4.8 g., 48 mmole) in water (40 ml.) was acidified to pH 5 with 5N hydrochloric acid. 2-Deoxy-D-ribose (3.0 g., 27.5 mmole) and sodium cyanoborohydride (1.35 g., 21.5 mmoles) were added and the solution was stirred and allowed to stand overnight at room temperature. The solution was basified to pH 10 with sodium hydroxide, washed several times with ethyl acetate to remove excess benzylamine, and acidified to pH 4 with hydrochloric acid. Methanol (60 ml.) was added and the crude mixture was hydrogenated at 50° C. and 50 p.s.i. in the presence of 10% palladium-on-charcoal catalyst, fresh catalyst being added after 24 hours. After a further 4 days, the solution was filtered and evaporated, the product being chromatographed on Amberlite CG 50 ion exchange resin ($NH_4^+$ form) eluting with 0.1N ammonium hydroxide to give 5-amino-1,2(S),3(S)-trihydroxy-pentane (1.6 g., 53%. m/e 135. $C_5H_{10}NO_3$ requires m/e 135.

(B) The product from (A), (1 g.), was dissolved in water (20 ml.) and sodium carbonate (2 g.) and a solution of p-nitrophenyl chloroformate (3 g.) in acetone (10 ml.) were added with stirring at 0° C. The solution was kept at 3° C. for 16 hours, then acidified with 5N hydrochloric acid and washed several times with ethyl acetate. The aqueous solution was evaporated and the residue was extracted with ethanol and chromatographed on a column of silica eluting with a gradient of chloroform/ethanol to give 6-(S)-(1',2'-dihydroxyethyl)tetrahydro-1,3-oxazin-2-one (0.65 g., 55%).

(C) The product from (B) (0.6 g., 3.7 mmole) was treated with a solution of periodic acid (1.0 g. 4.0 mmole) in water (5 ml.) adjusted to pH 5 with 5N sodium hydroxide. After 2 hours, the solution was filtered and the solvent evaporated; extraction with methano gave 6-(S)-dihydroxymethyl-tetrahydro-1,3-oxazin-2-one (0.35 g., 64%) as a colorless oil. m/e 100, $C_5H_9NO_4$—$CH(OH)_2$ requires m/e 100.

EXAMPLE 8

1-N-[(S)-4-Benzylamino-2-hydroxybutyl]Kanamycin A 3,3''-6'-Tri-N-formyl-kanamycin A (112 mg., 0.2 mmoles) dissolved in dioxan (5 ml.) and water (5 ml.) was treated with 3-benzyl-6-(S)-dihydroxymethyltetrahydro-1,3-oxazin-2-one (100 mg., 0.4 mmoles) and sodium cyanoborohydride (25 mg., 0.4 mmoles) and the pH of the mixture was adjusted to 6. The mixture was allowed to stand for 3 days at 40° C. 1N Sodium hydroxide solution (10 ml.) was then added and the mixture allowed to stand for a further 2 days at room temperature. The reaction mixture was then chromatographed on a column of Amberlite CG-50 ion exchange resin in the ammonium-ion form, eluting with a gradient of ammonium hydroxide from 0.05N to 0.3N. Fractions containing the desired product were combined and evaporated to yield 1-N-[(S)-4-benzylamino-2-hydroxybutyl]kanamycin A (96 mg.), $R_f$ 0.36.

Thin layer chromatography was performed on silica plates using a solvent system consisting of a 4:1:2 mixture of methanol, chloroform and 17% ammonium hydroxide. The spots were visualized after drying the plates by spraying with a 5% solution of t-butyl-hypochlorite in cyclohexane, drying the plates at 100° C. for 10 minutes in a ventilated oven, cooling and spraying with starch-potassium iodide solution. Kanamycin A gave an $R_f$ value of 0.16.

EXAMPLE 9

1-N-[(R)-4-Benzylamino-2-hydroxybutyl]kanamycin A

The procedure of Example 8 is repeated, except that the 3-benzylamino-6(S)-dihydroxymethyltetrahydro-1,3-oxazin-2-one is replaced by an equal amount of 3-benzylamino-6(R)-dihydroxymethyltetrahydro-1,3-oxazin-2-one. This affords the title compound.

EXAMPLE 10

1-N-[(S)-4-Amino-2-hydroxybutyl]kanamycin A

The product from Example 8 (40 mg.) was dissolved in an equipart mixture of methanol, water and glacial acetic acid (30 ml.) and hydrogenated at a pressure of 60 p.s.i. and 60° C. over 30% palladium-on-charcoal catalyst. After 8 hours the solution was filtered and evaporated and the residue chromatographed on Amberlite CG-50 ion exchange resin as previously described to yield 1-N-[(S)-4-amino-2-hydroxybutyl]kanamycin A (19 mg.) identical with a reference sample prepared as described in West German Offenlegungsschrift No. 2,547,738,

EXAMPLE 11

The procedure of Example 8 is repeated, except that the 3,3'',6'-tri-N-formylkanamycin A is replaced by an equivalent amount of:
kanamycin,
6'-N-methylkanamycin A,
3,3'',6'-tri-N-formyl-6'-N-methylkanamycin A,
3,3'',6-tri-N-formyl-6'-N-ethylkanamycin A and
3,3'',6'-tri-N-formyl-6'-N-butylkanamycin A,
respectively. This affords:
1-N-[(S)-4-benzylamino-2-hydroxybutyl]kanamycin A,
1-N-[(S)-4-benzylamino-2-hydroxybutyl]-6'-N-methylkanamycin A,
1-N-[(S)-4-benzylamino-2-hydroxybutyl]-6'-N-methylkanamycin A,
1-N-[(S)-4-benzylamino-2-hydroxybutyl]-6'-N-ethylkanamycin A and
1-N-[(S)-4-benzylamino-2-hydroxybutyl]-6'-N-butylkanamycin A,
respectively.

EXAMPLE 12

Hydrogenation of:
1-N-[(S)-4-benzylamino-2-hydroxybutyl]-6'-N-methylkanamycin A,
1-N-[(S)-4-benzylamino-2-hydroxybutyl]-6'-N-ethylkanamycin A and
1-N-[(S)-4-benzylamino-2-hydroxybutyl]-6'-N-butylkanamycin A,
respectively, according to the procedure of Example 10, affords the following congeners:
1-N-[(S)-4-Amino-2-hydroxybutyl]-6'-N-methylkanamycin A,
1-N-[(S)-4-Amino-2-hydroxybutyl]-6'-N-ethylkanamycin A and
1-N-[(S)-4-Amino-2-hydroxybutyl]-6'-N-butylkanamycin A,
respectively.

EXAMPLE 13

1-N-[(S)-3-Amino-2-hydroxypropyl]kanamycin A

A solution of 3,3'',6'-tri-N-formyl-kanamycin A (85 mg.), 5-(S)-dihydroxymethyl-1,3-oxazolidin-2-one (40 mg.) and sodium cyanoborohydride (20 mg.) in 50% aqueous methanol (2 ml.) was kept at 50° C. for 72 hours. The solution was acidified with 3N hydrochloric acid and after 24 hours was chromatographed on a column of Amberlite CG-50 ion exchange resin eluting with a gradient of aqueous ammonium hydroxide of increasing concentration. The isolated product was treated with 1N sodium hydroxide and after 24 hours at room temperature the solution was neutralized and chromatographed as before to yield 1-N-[(S)-3-amino-2-hydroxypropyl]kanamycin A (67 mg., 79%) identical by thin layer chromatography with a reference sample prepared according to the method disclosed in West German Offenlegungsschrift 2,547,738.

m/e (field desorption) gave M + 1 = 558. $C_{21}H_{43}N_5O_{12}$ requires M + 1 = 558.

EXAMPLE 14

1-N-[(R)-3-Amino-2-hydroxyethyl]kanamycin A 3,3'',6'-Tri-N-formylkanamycin A is reductively alkylated with 3-benzyl-5(R)-dihydroxymethyl-1,3-oxazolidin-2-one and sodium cyanoborohydride, and then hydrolyzed with 1N sodium hydroxide, according to the procedure of Example 13, to give 1-N-[(R)-3-benzylamino-2-hydroxyethyl]kanamycin A. The latter compound is catalytically hydrogenolysed, using the procedure of Example 10, to give 1-N-[(R)-3-amino-2-hydroxyethyl]kanamycin A.

EXAMPLE 15

1-N-[(S)-3-Amino-2-hydroxypropyl]kanamycin B

1-N-[(S)-3-Amino-2-hydroxypropyl]kanamycin B was prepared in a similar manner to that described in Example 8, but starting with 2',3,3'',6'-tetra-N-formyl-kanamycin B. Rf 0.53 in 3M sodium chloride (kanamycin B 0.85).

EXAMPLE 16

3,3'',6'-Tri-N-formyl-kanamycin A (0.45 g., 0.8 mmole) was dissolved in water (5 ml.) and 6-(S)-dihydroxymethyl-tetrahydro-1,3-oxazin-2-one (0.28 g., 2 mmole) and sodium cyanoborohydride (0.28 g., 4.5 mmole) were added. The solution was acidified to pH 6 and kept at 40° C. for 4 days. Chromatography on Amberlite CG-50 ion exchange resin eluting with 0.02N ammonium hydroxide gave 1-N-[tetrahydro-1,3-oxazin-2-on-6(S)-ylmethyl]-3,3'',6'-tri-N-formylkanamycin A (0.25 g., 48%). This product was dissolved in methanol (3 ml.) and 2N sodium hydroxide (3 ml.) was added. The solution was kept at room temperature for 48 hours, neutralized and chromatographed as described in Example 8 to yield 1-N-[(S)-4-amino-2-hydroxybutyl]-kanamycin A identical with a reference sample.

EXAMPLE 17

1-N-[(S)-4-Benzylamino-2-hydroxybutyl]-kanamycin A

A solution of 3,3'',6'-Tri-N-formyl-kanamycin A (0.57 g., 1 mmole) and 3-benzyl-6-[S]-dihydroxymethyl-tetrahydro-1,3-oxazin-2-one (0.47 g., 2 mmoles), dissolved in a mixture of methanol (11 ml.) and water (3 ml.), was hydrogenated at a pressure of 50 p.s.i. and 50° C. in the presence of a mixture of 10% platinum oxide on charcoal and 10% palladium oxide on charcoal (0.1 g.). When hydrogen uptake was complete the solution was filtered and evaporated to dryness. The residue was dissolved in 1N aqueous sodium hydroxide (14 ml.) and the solution was heated at 60° C. for 18 hours. After neutralizing and evaporating to a small volume the product was chromatographed on Amberlite CG-50 ion exchange resin as described in Example 8 to give the title compound.

What is claimed is:

1. A compound of the formula:

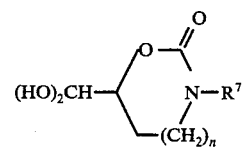

wherein $R^7$ is selected from the group consisting of hydrogen and benzyl, and $n$ is 0 or 1.

2. A compound according to claim 1, wherein $n$ is 1.

3. A compound according to claim 2, wherein $R^7$ is hydrogen.

4. The compound according to claim 3, wherein the carbon atom to which the $(HO)_2CH-$ group is attached has the (S)-configuration.

5. A compound according to claim 2, wherein $R^7$ is benzyl.

6. The compound according to claim 5, wherein the carbon atom to which the $(HO)_2CH-$ group is attached has the (S)-configuration.

* * * * *